United States Patent [19]

Gressick et al.

[11] Patent Number: 4,764,242

[45] Date of Patent: Aug. 16, 1988

[54] ADHESIVE APPLYING APPARATUS

[75] Inventors: Joseph A. Gressick, DePere; Randall B. Korth, Green, both of Wis.

[73] Assignee: The Kendall Company, Boston, Mass.

[21] Appl. No.: 944,054

[22] Filed: Dec. 18, 1986

[51] Int. Cl.[4] .................................................. B31F 1/22
[52] U.S. Cl. ..................................... 156/494; 118/315; 118/323; 156/550; 156/578
[58] Field of Search .................. 156/578, 356–358, 156/164, 229, 291, 548, 550, 543, 494; 118/216, 219, 221, 222, 669, 674, 680, 681, 315, 323, 242

[56] References Cited

U.S. PATENT DOCUMENTS

| 4,369,613 | 1/1983 | Gess | 156/548 X |
| 4,482,579 | 11/1984 | Fujii et al. | 118/315 X |
| 4,495,890 | 1/1985 | Nikkel | 118/674 |
| 4,618,384 | 10/1986 | Sabee | 156/205 |
| 4,675,068 | 6/1987 | Lundmark | 156/494 X |

*Primary Examiner*—David Simmons
*Attorney, Agent, or Firm*—Donald N. Halgren

[57] ABSTRACT

A machine for applying continuous bands of adhesive generally longitudinally along an absorbent pad, which pad may comprise a diaper or an adult incontinent brief. The machine includes a pair of adhesive ejecting nozzles which direct adhesive onto the backing sheet of the pad as the sheet is moved therepast. The nozzles are intermittently directed to their respective sides, under control of a counting apparatus, so as to effectuate a pair of non-linear bands of adhesive onto the sheet. A pair of elastic bands are guided onto the sheet so as to attach themselves only in intermediate portions of the adhesive bands on the backing sheet. The nozzles are also withdrawable from the backing sheet when the sheet is not moving, so as to prevent their burn through. The nozzles movement is controlled by piston and cylinder units under solenoid regulation, which has received signals from the counting apparatus.

13 Claims, 5 Drawing Sheets

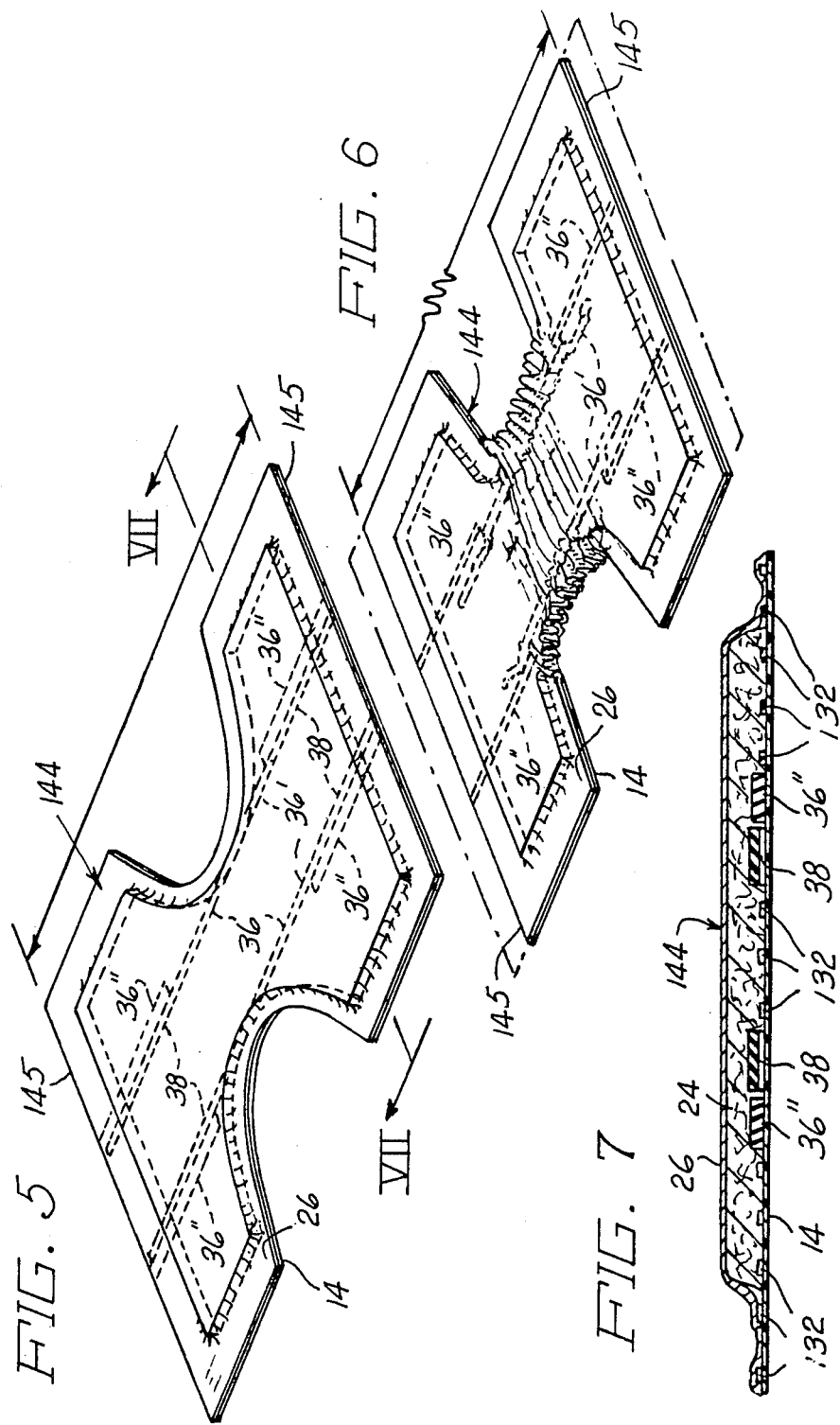

ADHESIVE APPLYING APPARATUS

BACKGROUND OF THE INVENTION (1) Field of the Invention

This invention relates generally to the apparatus useful in the manufacture of absorbent pads, and more particularly to the apparatus for applying adhesive to those absorbent pads.

2. PRIOR ART

Elastic ribbon should be applied in a stretched condition to the leg portions of absorbent undergarments such as babies' diapers or adult continent briefs. The elastic ribbon is applied in a stretched conditior only in that leg portion so as to cause gathers therein. The remaining portion of the elastic extending over the balance of the absorbent pad is not adhered to the pad, so that that portion of the pad will not gather. In the manufacture of diapers and absorbent pads as well as adult incontinent briefs, an elastic band in continuous form is placed against an unrolled web or a continuous web or backing material. The elastic band has adhesive applied thereon in discontinuous portions therealong, so as to effectuate the attachment of the bands to the backing material along the leg portions thereof. Such an apparatus and method for same is shown for example, in U.S. Pat. No 4,081,301. Adhesive, as shown in this Patent, may be applied in thin strands on the elastic or as individual dots of adhesive on the elastic. The elastic band is then applied to diaper material as the diaper material proceeds along the assembly processes. As the individual backing sheets are cut and severed from one another, the stretched elastics are also severed. The portion of the elastics that are glued or bound by adhesive to the backing sheet of the diaper cause the diaper in that portion to gather. The unattached portions of the rubber band merely remain in the flaccid state adjacent the absorbent pad. U.S. Pat. No. 4,371,417 shows an apparatus for inserting elastic strips onto diapers for stretching and relaxing predetermined lengths of the elastic strips as they are secured to the diaper material. U.S. Pat. No. 4,297,157 shows a rather complicated apparatus for placing elastic strips under tension, onto garments. An annular array of linkages and arms are used to apply the elastic to discrete areas adjacent the leg openings of diapers.

Another Patent showing the adhesion of elastic to disposable diapers is shown in U.S. Pat. No. 4,585,507. An oscillating fork means V-folds longitudinally spared portions of an adhesive equipped ribbon against the backing sheet of a diaper. The V-shaped longitudinally spaced portions do not adhere to their respective portions of diaper and so fail to cause the required gathering thereof. U.S. Pat. No. 4,578,133 shows a method and apparatus for applying strips of elastic to a web of diaper material. The apparatus is very complicated and requires a difficult method of applying the strips to the web of material. Two other recent disclosures are shown in U.S. Pat. No. 4,572,043 and 4,574,022 which again also show rather complicated apparatus for applying discrete lengths of elastic material to a moving web of backing sheet. In U.S. Pat. No. 4,525,229 an elastic band is attached to a tape which is attached to the web forming the backing sheet of the diaper. U.S. Pat. No. 4,556,596 shows self adhering elastic strips applied to a flexible base material. U.S. Pat. No. 4,543,141 shows another arrangement for longitudinally folding portions of the ribbon prior to its disposition against a base sheet to immobilize those portions of the ribbon. U.S. Pat. No. 4,523,969 shows an arrangement for gripping elastic ribbon at several points and stretching same prior to its application against a base sheet comprising the bottom portion of the diaper. U.S. Pat. No. 4,507,163 shows a method of feeding adhesive onto an elastic before it is applied to the base of a diaper.

Though the collection of prior art is numerous, and often very complicated, none of it appreciates a simpler apparatus for the application of adhesive onto a backing sheet of an absorbent pad.

Thus it is an object of the present invention to provide an apparatus for permitting the attachment of elastic to a web not shown in the art.

BRIEF SUMMARY OF THE INVENTION

The present invention provides for continuously attaching continuous lengths of elastic ribbon to a moving web of indeterminate length. The elastic ribbon is of continuous length, and is applied against a continuous strip of adhesive placed upon the moving web. The continuous strip of adhesive is applied on a nonlinear manner to the moving web. The web which may comprise the back sheet of a diaper or an adult incontinent brief, or the like, is caused to move about on a rotatable roller or drum. Subsequent to the web moving on the roller it is caused to travel upon a conveyor belt where it meets an upper layer of fluff material and a topmost layer. As the web moves around the roller, a pair of adhesive ejection nozzles apply a continuous strip of adhesive directly to the moving web. The nozzles are shifted transversely during the application of the strip of adhesive onto the moving web so as to effect a generally stepped or "sinusoidal" pattern of adhesive thereon.

The method of the present invention comprises feeding an elastic ribbon to an assembly station in a stretched condition; supplying a continuous web of material such as backing sheet to an assembly station in a tensioned condition; feeding an elastic ribbon to the assembly station in a stretched condition; applying adhesive in a continuous manner to the web of material; moving transversely the adhesive application nozzles while said web is moving; returning said adhesive applying nozzles to their original position while said web is moving; and timing the movement of the adhesive applying nozzles in conjunction with the speed of the moving web so as to properly effectuate a generally stepped repetitive pattern of adhesive thereon. Finally, the elastic ribbons are attached to portions of the adhesive bands that is applied to the backing sheet as it goes around the roller.

The apparatus at the assembly station for manufacturing the absorbent web of material comprises a rotatable roller or drum supported on an axis. The rotatable drum has a first idler roll supported thereabove. A web of backing material of a indeterminate length is disposed over the first idler roll and around the drum. The web of material is continued over a second idler roll and arranged to be continuously transported on a conveyor belt on which it receives a layer of absorbent fluff material and a top sheet. An adhesive applying mechanism is disposed adjacent the drum so as to apply a pair of continuous strips or bands of adhesive against the web as it wraps around the drum.

The adhesive applying mechanism comprises a lower frame. The lower frame consists of a pair of upstanding legs across which is disposed a transverse mounting plate. The mounting plate is generally parallel to the axis of the drum. A first moving means is fixedly attached to the generally mid-portion of the mounting plate and is attached to the movable portion of the first moving means. The moving means may comprise a double acting air cylinder. A middle plate is movedly disposed above the mounting plate. A support means is arranged on each end of the middle plate. The support means permits the middle plate to be moved transversely with respect to the mounting plate therebeneath. A linkage is arranged between the double acting air cylinder and the middle plate so as to effect said movement.

A pair of upper plates are movably supported on the middle plate. Each upper plate carries an adhesive nozzle. Each upper plate is adjustably movable generally longitudinally, with respect to the middle plate. Each upper plate has a manual adjustment means so as to permit the setting of the initial location of the upper plate with respect to the middle plate. Each upper plate has a second moving means thereon, such as a double acting pressure cylinder therewith. The pressure cylinder may be attached to the adhesive nozzle by a connecting rod. Each adhesive nozzle is permitted to slide transversely with respect to the upper plate. Each pressure cylinder on the upper plate is connected by proper means to a solenoid valve means which effectuates enactment of transverse movement of the adhesive nozzles with respect to the upper plates on which they are slidably disposed.

The first moving means on the lower mounting plate is connected to a pressurizable source controlled by a solenoid valve for actuating the air cylinder therewith. The first moving means effectuates movement of the middle plate and therefore the movement of the adhesive nozzles radially toward and away from the drum on which the web is carried. The adhesive nozzles, being heated, are of necessity moved away from the web of material when the web of material has stopped moving, so as to prevent any burn through thereof. A proper control system effectuates the timing of the second moving means so as to control the transverse movement of the adhesive nozzles while they are depositing a strip of adhesive onto the web or backing sheet of material as it is moved about the drum. A pair of arms extend down from the transversely movable upper plates. At the distal end of each arm there is disposed a pulley. The pulley guides the elastic strip from its supply roll to its linear disposition on the adhesive strip and sequentially, to the non-adhesive portion of the web or backing sheet.

When each of the adhesive nozzles have moved transversely outwardly from one another, they are still caused to continuously deposit the strip or bands of adhesive out of the normal path of the elastic bands. As the web of material is driven around the drum, and the elastic bands are held thereagainst, that portion of the elastic bands which are not in overlying contact with the adhesive strip on the web, will not stick to the web. Therefore the elastic band in those noncontacting, nonadhering areas will not cause the absorbent material to "gather" thereon when the elastic band has been cut and when it returns to its relaxed state.

The absorbent pad manufactured by the apparatus and method described hereabove has a pair of adhesive strips which run generally longitudinally with the length of the pad. The adhesive strips or bands form a generally repetitively "stepped" configuration, the adhesive acting to secure the fluff layer against the bottom layer of the pad, where the adhesive is not contacting any elastic band. The adhesive thereby also acts as a fluid barrier to help minimize fluid migration into the side flaps of the pad, diaper or brief. The fluid, such as urine, is thereby directed along the mid-portion of the pad, helping to minimize leakage and uncomfortability in the pad.

BRIEF DESCRIPTION OF THE DRAWINGS

The objects and advantages of the present invention will become more apparent, when viewed in conjunction with the following drawings, in which:

FIG. 5 shows a perspective view of an absorbent pad indicating the pattern of adhesive strip thereon and the elastic band thereattached;

FIG. 6 shows a perspective view of the absorbent pad of FIG. 5, in an unstretched state; and FIG. 7 is a view taken along the lines VII—VII of FIG. 5.

DESCRIPTION OF THE PREFERRED EMBODIMENTS

Figure 1:
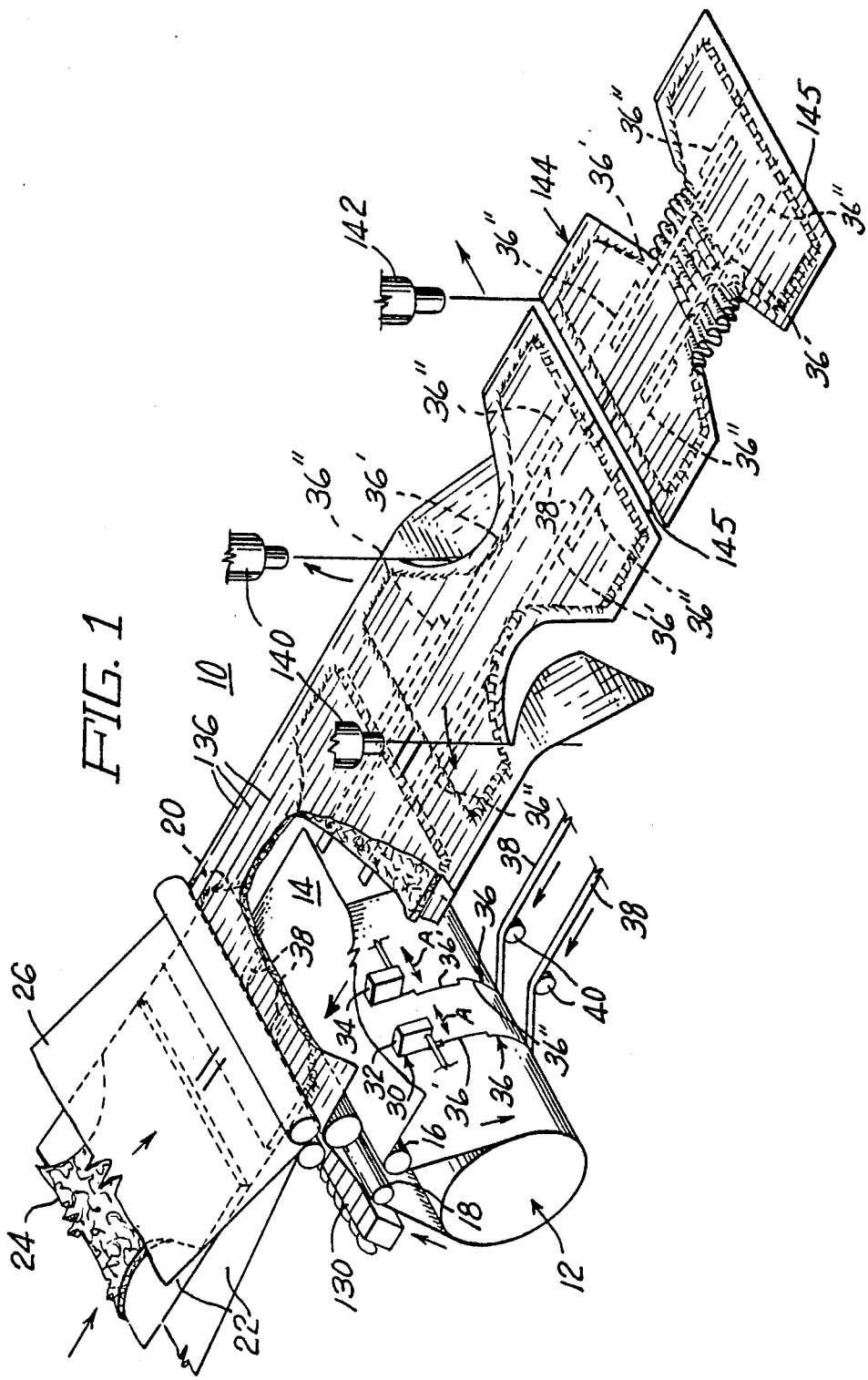
FIG. 1 is a perspective view of an assembly station of the present invention having a pair of oscillatable glue guns shown disposed against a backing sheet.

Referring to the drawings in detail, and particularly to FIG. 1, there is shown an assembly station 10, utilizable in the manufacture of absorbent pads such as baby diapers or adult incontinent briefs. This application incorporates by reference, copending commonly assigned U.S. patent applications Ser. Nos. P.F. 1639 and P.F. 1640 entitled Method of Applying Adhesive and Adhesive Applying Apparatus respectively, showing this absorbent pad.

A rotatable roller or drum 12 is shown in perspective, in FIG. 1, having a web 14 of indeterminate length, comprising "backing material" movably disposed therearound. The web 14, moving in a direction as indicated by the arrows thereon, is coming from a source, such as a supply roll, not shown. The web 14 first passes over a first idler roll 16, before it wraps around the drum 12. The web 14 then passes over a second idler roll 18 before it begins its journey on a main conveyor belt system 20, only a portion being shown for clarity.

A feed conveyor belt system 22, is shown on the left, in FIG. 1, wherein a layer of absorbent fluff material 24 and a liquid permeable top sheet 26 are juxtaposed in contacting overlying relationship with the web 14 of backing material. The web 14 of backing material is made of a plastic or like liquid-impermeable material.

A primary adhesive applying mechanism 30, comprising a pair of movable nozzles 32 and 34, are arranged so as to apply a generally stepped array of adhesive portions comprising a non-linear strip of adhesive 36 on the web 14 as it winds around the drum 12. A pair of arrows "A" show the transverse motion available to the movable nozzles 32 and 34. Only the nozzles 32 and 34 of the adhesive applying mechanism 30 are shown for clarity, in FIG. 1.

A pair of elastic bands 38 is shown, being guided over a pair of pulleys 40. The pulleys 40 are rotatively held on the lower ends of a pair of arms 41. As the drum 12 is caused to rotate (clockwise as shown in the drawings), the elastic bands 38 are caused to be pressed against portions of the strip of adhesive 36 already deposited on the advancing web 14. The elastic bands 38 are thus fixedly attached only to those linear portions of the web 14, where the adhesive strips 36 are in line with the elastic bands 38, such as the linear strip of adhesives shown in FIG. 1 at 36'. The elastic bands 38, being held in a linear manner as the drum 12 rotates, comes into non-adhering contact with the web 14 (backing sheet), because the strip of adhesive 36, such as indicated by 36" is not in contact or alignment therewith, by virtue of the movable nozzles 32 and 34 having been actuated to their respective sides (left and right).

Figure 2:
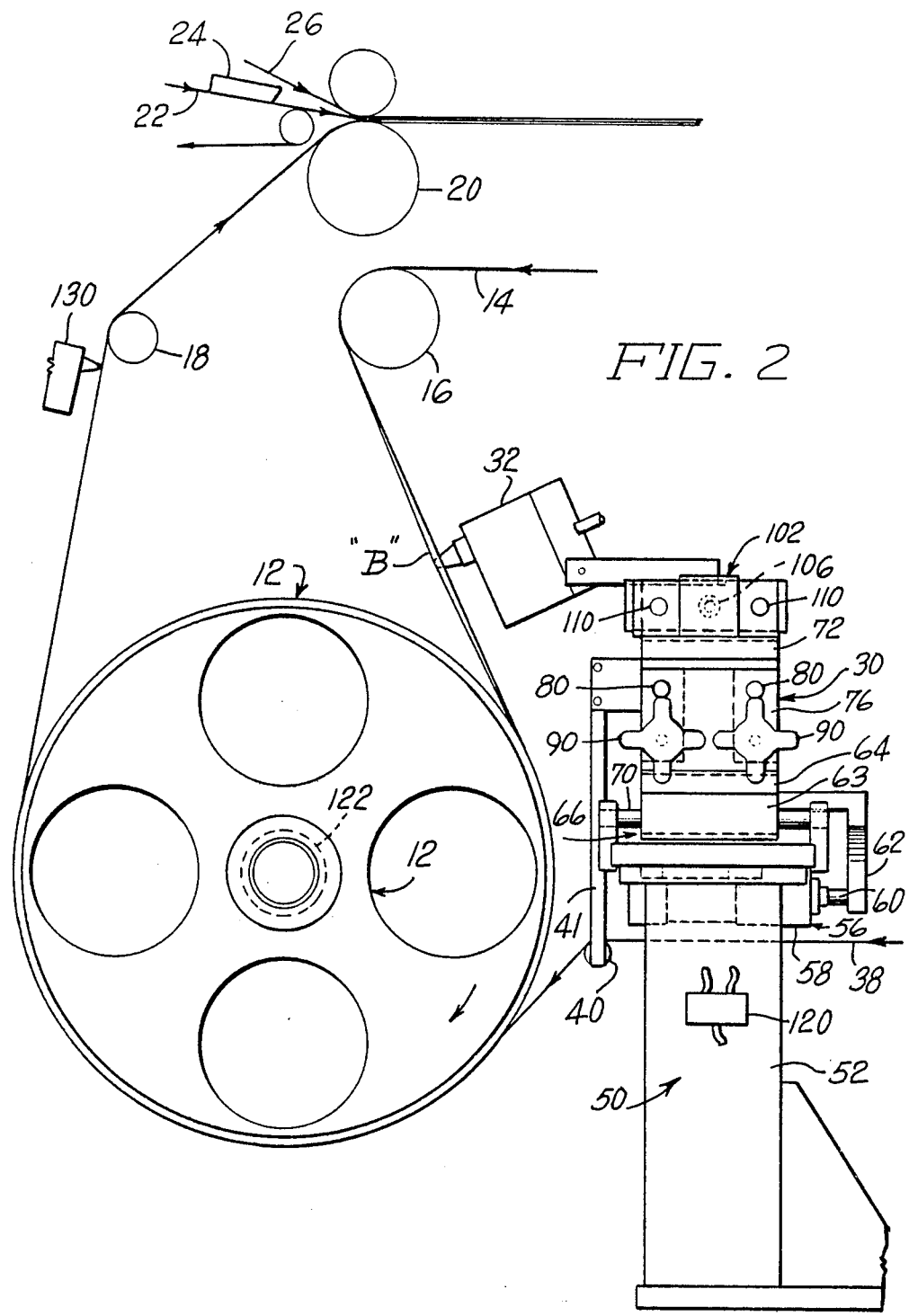
FIG. 2 is an elevational view of the end of the drum and adhesive application apparatus.
Figure 3:
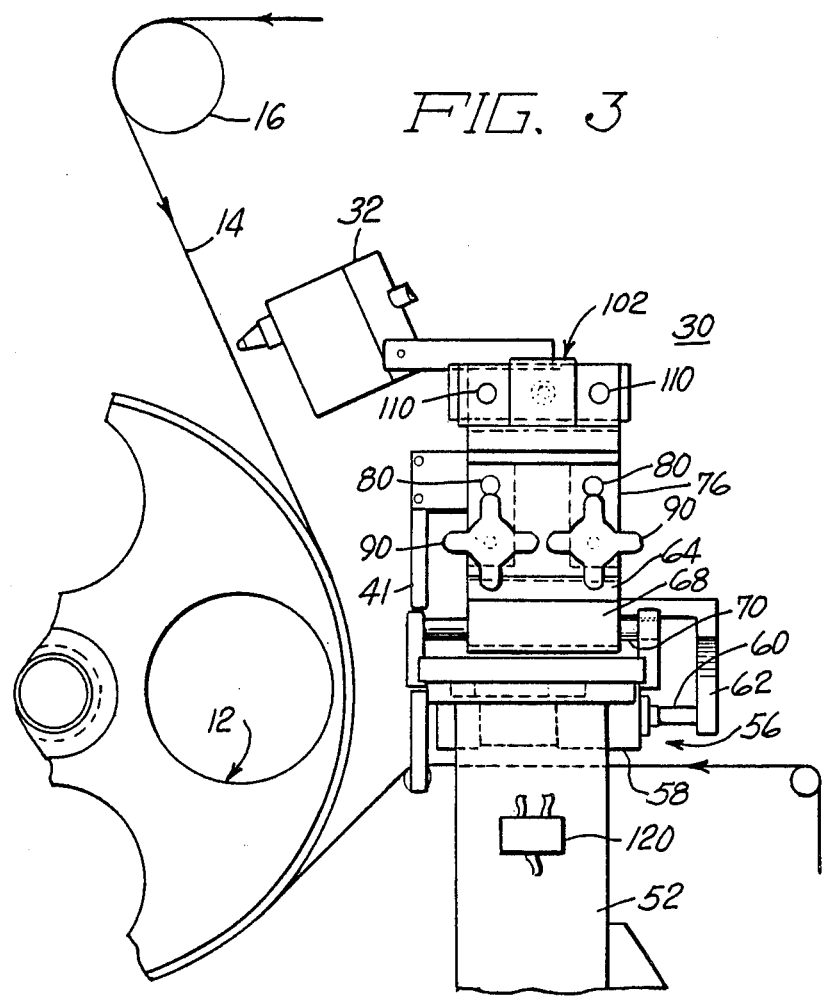
FIG. 3 is a view similar to FIG. 2, with the application apparatus moved away from the drum.
Figure 4:
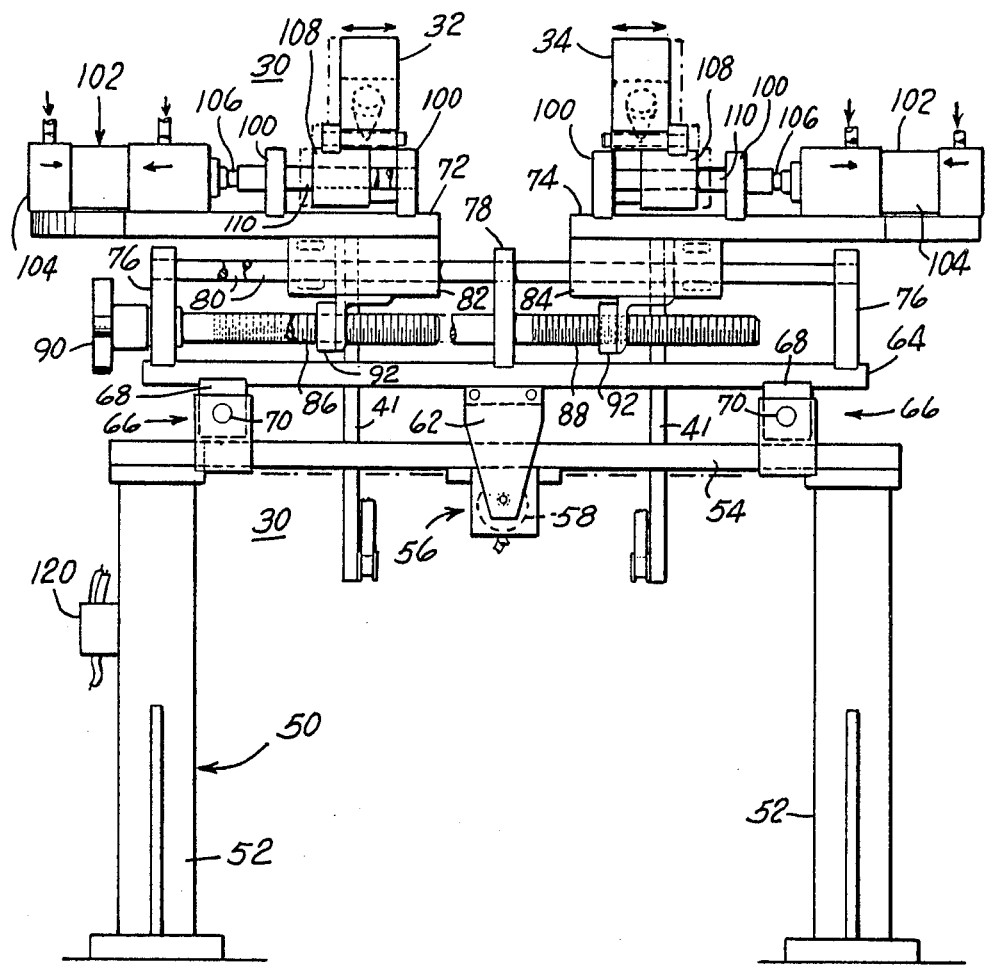
FIG. 4 is a side elevational view of the adhesive application apparatus.

The adhesive applying mechanism 30 is shown more clearly in FIGS. 2, 3 and 4. The mechanism 30 is elongated, and as such, is generally parallel to the axis of rotation of the drum 12. The adhesive applying mechanism 30 has a lower frame 50, having a pair of upstanding legs 52, across which there is disposed, a transverse mounting plate 54. The mounting plate 54 is shown most clearly in FIG. 4. A first moving means 56 is secured to the mid-portion of the mounting plate 54. The first moving means 56 may comprise a double-acting pressurizable cylinder 58, having a piston rod 60 extending therefrom. The piston rod 60 is attached to a bracket 62 extending downwardly from a middle plate 64. A support means 66, is arranged on each end of the middle plate 64. Each support means 66 comprises a slider 68 arranged to move back and forth on a bar 70.

A pair of upper plates 72 and 74 are movably supported above the middle plate 64. An end frame 76 extends upwardly from each end of the middle plate 64, and a guide frame 78 extends upwardly from the middle of the middle plate 64. A pair of slide shafts 80 are arranged between the end frames 76 and extend through the guide frame 78. Each upper plate 72 and 74 has a housing 82 and 84 respectively which is supported on and slides upon the slide shafts 80. A pair of rotatable threaded shafts 86 and 88 are disposed through one end frame 76 on one side of the middle plate 64, as shown in FIG. 4. Each threaded shaft 86 and 88 has a handle 90, by which they may be rotated. A captive nut 92 is secured to the bottom of each housing 82 and 84. Rotation of the handles 90, will rotate each threaded shaft 86 and 88, each with respect to its captive nut 92, so as to cause sliding movement, for transverse manual adjustment, of the upper plates 72 and 74 and hence their respective nozzles 32 and 34, with respect to the middle plate 64. Each arm 41 supporting the pulleys 40 are attached at their upper end, to one of the upper plates 72 or 74. Adjustment of the nozzles 32 and 34, by adjustment of the handles 90, will concomitantly adjust the horizontal location of the pulleys 40, and thereby, the location of the elastic bands 36.

Each nozzle 32 and 34 is also arranged for transverse sliding movement on their respective upper plates 72 and 74. A pair of nozzle support frames 100 extend upwardly from each upper plate 72 and 74.

A nozzle shifting means 102 is arranged on each upper plate 72 and 74 to effectuate the transverse movement of the nozzles 32 and 34 thereon. The shifting means 102 in this embodiment preferably comprises a pressurizable double acting piston and cylinder unit 104 secured to the distalmost ends of each upper plate 72 and 74. A piston rod 106 extends movably through its outermost respective support frame 100. The piston rod 106, is attached at its distalmost end, to a piston rod extension 107. The piston rod extension 107 is attached at its distalmost end to a nozzle bracket 108. A pair of nozzle support rods 110 are arranged between each pair of nozzle support frames 100. The nozzle brackets 108 each slide on their respective nozzle support rods 110.

Each nozzle 32 and 34 has a heating element, not shown, arranged therewithin, so as to maintain the adhesive supplied thereto, in a fluid state. Each nozzle 32 and 34 has proper adhesive supply means, under pressure, to permit a continuous ejection of adhesive onto the "backing" sheet web 14 as it moves therepast.

Each piston and cylinder unit 104 is connected through proper means, not shown, to a regulator 120, such as a solenoid valve arrangement. The regulator 120 provides the means for controllably shifting each adhesive nozzle 32 and 34 transversely, so as to effectuate the non-linear (almost sinusoidal) stepped pattern of adhesive onto the web 14. The regulator 120, which provides the pressure to the proper portion of the piston and cylinder units 104, is controlled by a signal generator means 122, which is arranged on the drum 12. The signal generator means 122 sends signals to a counter, not shown, which provides the input to the regulator 120, switching the valving therein to effectuate proper transverse movement of the nozzles 32 and 34. The regulator 120 may also effectuate energization of the first moving means 56 to cause the middle plate 64 to move toward or away from the drum 12 and web 14. This is presented in FIG. 3, wherein the nozzle 32 is shown withdrawn from the surface of the web 14. Whenever the web 14 is not moving, a signal may be sent to the regulator 120 to pressurize the piston-cylinder units 58 to move the nozzles 32 and 34 away from the web 14, so that they will not burn through or melt the plastic (typical) web 14. When the web 14 is actually moving, the nozzles 32 and 34 are pressed slightly against the web 14 for positive contact, as shown by the slight bulge "B" in the web 14, in FIG. 2.

A secondary arrangement of adhesive applying nozzles 130 is shown in FIGS. 1 and 2. The secondary nozzles 130 distribute a linear array of thin strands of adhesive 132 across the entire web 14 as shown in FIGS. 1 and 7. The thin strands of adhesive 132 are utilized to help secure the layer(s) of fluff 24 against the web 14 (backing sheet), and to secure the peripheral portions of the top sheet 26 to the web 14 (backing sheet).

The assembly of absorbent pads such as diapers and adult incontinent briefs is shown in a somewhat simplified manner in FIG. 1. The fluff 24, having an "hour glass" configuration, which defines the "leg" portions, is secured between the "backing" sheet web 14 and the upper layer or top sheet 26, as they proceed onto the main conveyor belt system 20. At this conjuncture, the elastic bands 38 are still maintained in a "stretched" condition while the adhesive that portion of the elastic bands are placed against sets. A leg area cutting means 140, performs a cutting operation on the backing web 14 and the upper sheet 26 so as to create the "hourglass" configuration on all the remaining layers of the absorbent pad.

A transverse cutting means 142 makes a cut across the continuous line of layers of web 14, fluff 24 and top sheet 26 at proper timed intervals to define a "waist" edge 145, and to create individual absorbent pads 144, such as diapers or adult incontinent briefs from the oncoming indeterminate length of same proceeding down the conveyor system 20.

Once the transverse cut has been made, the elastic bands 38 are no longer under tension in that portion of the elastic bands 38 which was placed over the adhesive 36' which was in alignment therewith, and thus contracts to form "gathers" in the absorbent pad 144, as shown on the right hand side of FIG. 1 and in FIG. 6. The remaining "ends" of the elastic band 38 merely becomes loose and flaccid.

The remaiing adhesive 36 to which no elastic band is attached, provides a strong bond with the fluff 24, as shown in FIG. 7. This bond with the fluff 24 extends in a generally parallel manner up both sides of the absorbent pad 144, to the waist edge 145. That extended band of adhesive 36" becomes a moisture dam to facilitate directional flow of urine away from the sides of the abosorbent pad 144 where it might tend to leak.

Thus the continuous non-linear band of adhesive arranged on the backing sheet of the absorbent pad 144 provides a multiple function. It permits the elastic band 38 to be adhered to the pad where it is necessary, thus providing the "gathers" therein for snug fit around a wearer's legs, while also permittting a liquid damming function to occur, so as to direct urine from potential areas which are prone to leakage.

We claim:

1. A machine for the application of continuous non-linear bands of adhesive onto a moving web for an absorbent pad construction, comprising:
   a frame assembly for supporting adhesive application apparatus adjacent a web;
   a first generally horizontally disposed support arranged across a pair of frame members for moving said adhesive application apparatus toward and away from a web;
   a second support arrangement for moving said adhesive applications apparatus transversely with respect to a web;
   a guide support means for guiding a continuous elastic band against said web to adhere to portions of said adhesive applied thereon;
   said support arrangement comprising an intermediate support slidably disposed over said frame assembly, with a first moving means arranged therebetween to effectuate any said moving;
   said second support arrangement comprising at least one support plate mounted on said first support arrangement;
   a threadable adjustment means disposed between said first support and said support plate to permit desired locating alignment of said adhesive application apparatus;
   said support plate arrangement having a nozzle shifting means arranged thereon to move said adhesive application apparatus with respect to said plate support arrangement;
   said nozzle shifting means comprising a piston and cylinder unit secured to said support plate, having a piston rod attached to said adhesive application apparatus to effectuate transverse moving thereof;
   said support plate also having a pair of nozzle support rods on which said adhesive application apparatus is permitted to slide; and
   a regulator for controlling said piston and cylinder units for proper pressurized sequence of operations, thus effectuating shifting of said adhesive applicators from one path to another, to permit the disposition of non-linear bands of adhesive on a web moving thereadjacent.

2. A machine as recited in claim 1, wherein said guide support means comprises a pulley disposed on a rigid arm, which rigid arm is secured to said second support means.

3. A machine as recited in claim 1, wherein said first moving means comprises a pressurizable piston and cylinder unit arranged between said first support and said frame assembly.

4. A machine as recited in claim 1, wherein said first support arrangement has a support means at each end thereof to facilitate sliding of said first support arrangement on said frame assembly.

5. A machine as recited in claim 1, wherein said second support arrangement comprises a pair of support plates, each of said support plates being manually movable by said threaded adjustment means so as to permit initial alignment of said adhesive apparatus with respect to a web.

6. A machine as recited in claim 1, including a drum about which a web is rotated, said drum having an axis which utilizes a counter mechanism therewith to send signals to said regulator to indicate the timing of movement of a web therepast.

7. A machine for the continuous application of a plurality of bands of adhesive onto a moving web, onto which a plurality of elastic bands will be partially attached, for partial gathering of the webs where said elastic bands are attached in an absorbent pad construction, said machine comprising:
   a pair of adhesive applicators movably supported on a support plate for applying adhesive onto a moving web for an absorbent pad;
   an intermediate support;
   a pair of manually adjustable means for locating said support plate on said intermediate support;
   a mounting plate supported on a frame for carrying said intermediate support;
   a first moving means for moving said intermediate support with respect to said mounting plate on said frame.

8. A machine as recited in claim 7, including: an elastic band support means which is attached to said mounting plate for concurrent transverse adjustment therewith.

9. A machine as recited in claim 8 having a moving means for actuating the transverse movement of said adhesive applicators to generate the non-linearity of the bands of adhesive applicable to a web moving therepast.

10. A machine as recited in claim 9 wherein said means for actuating transverse movement of said adhesive applicators comprises a counter mechanism adapted with a drum around which a web being acted upon, must travel, said counter providing proper timed signals to a valve means to permit the actuation of said moving means.

11. A machine as recited in claim 10, wherein said moving means comprises pressurizable piston and cylinder units arranged on said machine.

12. A machine for the application of a continuous band of adhesive onto a movable web for an absorbent pad construction, comprising:
   a frame for support a pair of adhesive ejecting nozzles;
   a means for moving each of said nozzles sideways while it ejects adhesive onto a web, causing bands of adhesive being applied to said web to be non-linear;

a means for moving said nozzles away from its operational location adjacent a web;

a means for securing a continuous elastic band to only portions of said bands of adhesive on a web for permitting the partial gathering of a web upon subsequently cutting of said web and elastic bands in an absorbent pad construction.

13. A machine as recited in claim 12, wherein said means for moving said nozzles comprises pressurizable piston and cylinder units actuatable from a valve means.

* * * * *